US010064922B2

(12) United States Patent
Balu-Iyer

(10) Patent No.: US 10,064,922 B2
(45) Date of Patent: Sep. 4, 2018

(54) COMPOSITIONS AND METHODS FOR IMMUNE TOLERANCE INDUCTION

(71) Applicant: The Research Foundation for The State University of New York, Amherst, NY (US)

(72) Inventor: Sathy V. Balu-Iyer, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 212 days.

(21) Appl. No.: 14/349,862

(22) PCT Filed: Oct. 8, 2012

(86) PCT No.: PCT/US2012/059223
§ 371 (c)(1),
(2) Date: Apr. 4, 2014

(87) PCT Pub. No.: WO2013/070362
PCT Pub. Date: May 16, 2013

(65) Prior Publication Data
US 2015/0004218 A1    Jan. 1, 2015

Related U.S. Application Data

(60) Provisional application No. 61/607,195, filed on Mar. 6, 2012, provisional application No. 61/543,859, filed on Oct. 6, 2011.

(51) Int. Cl.
| | | |
|---|---|---|
| A61K 39/00 | (2006.01) | |
| A61K 38/37 | (2006.01) | |
| A61K 9/127 | (2006.01) | |
| A61K 38/47 | (2006.01) | |
| A61K 47/69 | (2017.01) | |

(52) U.S. Cl.
CPC .......... *A61K 39/0005* (2013.01); *A61K 9/127* (2013.01); *A61K 38/37* (2013.01); *A61K 38/47* (2013.01); *A61K 47/6911* (2017.08); *C12Y 302/0102* (2013.01); *A61K 2039/577* (2013.01); *A61K 2039/6018* (2013.01)

(58) Field of Classification Search
None
See application file for complete search history.

(56) References Cited

U.S. PATENT DOCUMENTS

| | | | | |
|---|---|---|---|---|
| 5,573,779 | A * | 11/1996 | Sato | ........................ A61K 9/127 424/450 |
| 7,875,289 | B2 | 1/2011 | Balu-Iyer et al. | |
| 8,100,218 | B2 | 1/2012 | Case et al. | |
| 2005/0227913 | A1* | 10/2005 | Balasubramanian | ........................ A61K 9/1075 424/278.1 |
| 2009/0053297 | A1 | 2/2009 | Balu-Iyer et al. | |
| 2012/0164189 | A1* | 6/2012 | Balu-Iyer | ............... A61K 9/127 424/400 |

FOREIGN PATENT DOCUMENTS

| | | |
|---|---|---|
| WO | 2000/032223 A2 | 6/2000 |
| WO | 2007002886 | 1/2007 |
| WO | 2011/005850 A1 | 1/2011 |

OTHER PUBLICATIONS

Li et al. Contextual regulation of inflammation: a duet by transforming growth factor-beta and interleukin-10. Immunity. Apr. 2008;28(4):468-76.*
Moncef Zouali. Immunological Tolerance: Mechanisms. Encyclopedia of Life Sciences, 2001; 1-9.*
Hoffmann et al. Interaction between phosphatidylserine and the phosphatidylserine receptor inhibits immune responses in vivo. J Immunol 2005; 174:1393-1404.*
Chen et al. Phosphatidylserine Regulates the Maturation of Human Dendritic Cells. The Journal of Immunology, 2004, 173: 2985-2994.*
Ramani et al. Phosphatidylserine Containing Liposomes Reduce Immunogenicity of Recombinant Human Factor VIII (rFVIII) in a Murine Model of Hemophilia A. Journal of Pharmaceutical Sciences, vol. 97, 1386-1398 (2008). (Year: 2007).*

\* cited by examiner

*Primary Examiner* — Marcela M Cordero Garcia
*Assistant Examiner* — Jia-Hai Lee
(74) *Attorney, Agent, or Firm* — Hodgson Russ LLP

(57) ABSTRACT

Methods and compositions to reduce immunogenicity of proteins are disclosed. Compositions comprising therapeutic proteins (such as Factor VIII or any other protein or peptide) complexed with liposomes comprising PS and PC (PS liposomes), or comprising PS, PI and PC and, optionally, cholesterol (PS/PI liposomes) may be used.

8 Claims, 12 Drawing Sheets

Fig 5a & b

COMPOSITIONS AND METHODS FOR IMMUNE TOLERANCE INDUCTION

CROSS-REFERENCE TO RELATED APPLICATIONS

This application claims priority to U.S. Provisional Patent Application No. 61/543,859, filed Oct. 6, 2011, and to U.S. Provisional Patent Application No. 61/607,195, filed Mar. 6, 2012, the disclosures of which are incorporated herein by reference.

STATEMENT REGARDING FEDERALLY SPONSORED RESEARCH

This invention was made with government support under contract no. R01 HL-70227 awarded by the National Institutes of Health. The government has certain rights in the invention.

FIELD OF THE INVENTION

This invention relates generally to the field of immune intolerance for therapeutic proteins. More particularly, this invention relates to compositions and methods for induction of tolerance to immunogenic proteins.

BACKGROUND OF THE INVENTION

Immunogenicity against therapeutic proteins is a clinical issue and can greatly reduce safety and efficacy of protein based therapy. Antibody-based immune response can not only alter pharmacokinetics but also abrogate the pharmacological activity of the protein. There are several approaches that are undertaken to minimize immunogenicity including development of less immunogenic formulation, modifying treatment options, use of steroids and delivery approaches. Each approach has limitations and an effective approach to minimize immunogenicity has not been achieved.

In some instances, it has been observed that even if an individual is not immune intolerant during a treatment regimen, the individual may develop immune intolerance over time. In such instances, it would be desirable to develop approaches to suppress the later developed immune intolerance.

SUMMARY OF THE INVENTION

The present invention provides methods and compositions to reduce immunogenicity of proteins. The invention is based on the observation that administration of certain liposome compositions comprising the protein results in immunological hypo responsiveness against the protein for subsequent administrations.

The compositions of the present invention are complexes of a therapeutic protein and liposomes or lipid structures comprising phosphatidylserine (PS) and phosphatidylcholine and, optionally, phophatidylinositol (PI). The PI containing complexes may also, optionally, contain cholesterol. For example, the complexes can be Factor VIII bearing phosphatidylserine containing liposomes (FVIII-PS).

As used herein, the term protein-PS (such as FVIII-PS) means the protein is complexed to liposomes containing PS and PC. The term protein-PI (such as FVIII-PI) means the protein is complexed to liposomes containing PI and PC and, optionally, cholesterol. The term protein-PS/PI (such as FVIII-PS/PI) means the protein is complexed to liposomes containing PS, PI and PC and, optionally, cholesterol.

The present invention provides an administration strategy designated here as "inverse/reverse vaccination" strategy in which pre-exposure (i.e. immunization) to particular liposomal compositions (designated here as tolerogenic or priming compositions) comprising the protein can lead to hypo-responsiveness to the protein in subsequent challenge with free protein or less tolerogenic, or any other form of the protein (e.g., complexed to any other suitable carrier such as protein or peptide carriers or other carriers such as polyethylene glycol (PEG), surfactants, microspheres etc. The induction of immune tolerance is manifested as one or more of the following: down-regulated expression of co-stimulatory signals on dendritic cells, lowered CD4$^+$ T-cell proliferation and/or induced secretion of immuno-regulatory cytokines such as TGF-β and IL-10.

For example, administration of tolerogenic forms of FVIII (e.g., FVIII-PS and other lipid complexes such as FVIII-PS/PI) can lead to hypo-responsiveness to the protein in subsequent challenge with free protein or less tolerogenic forms of the protein, such as protein complexed to liposomes that do not contain PS, or protein complexed to a non-phospholipidic carrier.

Accordingly, the method of the present invention comprises administering a priming composition to an individual, said priming composition comprising the desired protein complexed to liposomes comprising phosphatidylserine (PS), or PS and phosphatidylinositol (PI), allowing the individual to develop immune tolerance, and then administering a second composition comprising free protein (without the liposome complexes) or comprising the protein complexed to liposomes in which the phospholipid composition is different from the phospholipid composition of the priming composition.

The method of the present invention can be used for individuals who are being administered the therapeutic protein but have not previously exhibited an immune intolerance to the protein, or for naïve individuals (i.e., those who have not been previously administered the peptide or protein). Individuals are deemed to not have exhibited immune intolerance to a protein if there are no detectable titers of antibodies to the protein The inverse vaccination strategy was tested in Hemophilia A, which is a bleeding disorder involving deficiency or dysfunction of Factor VIII. The complexes of the present invention showed reduction in the development of antibody response in Hemophilia A mice. Further, administration of these compositions down-regulated expression of co-stimulatory signals on dendritic cells, lowered CD4$^+$ T-cell proliferation and induced secretion of immuno-regulatory cytokines TGF-β and IL-10 under culture conditions, indicating induction of immunological tolerance. Such effects were not observed if the liposome complexes only contained PC or PG. The data demonstrates that inverse/reverse vaccination with a therapeutic protein leads to hypo-responsiveness upon re-challenge.

DETAILED DESCRIPTION OF THE INVENTION

Figure 1:
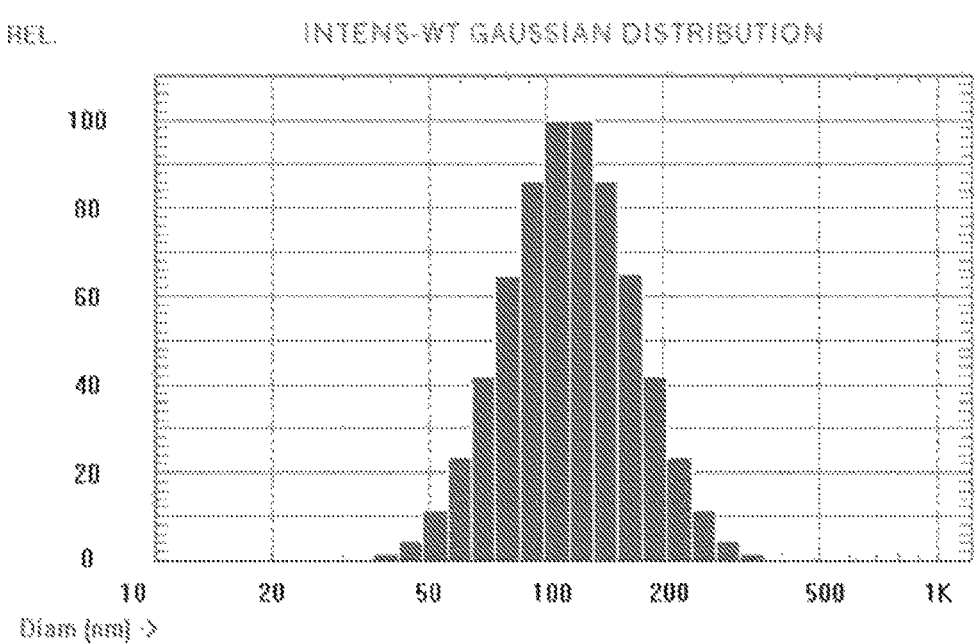
FIG. 1: A representation of particle size distribution of PS/PI/DMPC (30/30/40) liposomes as measured by dynamic light scattering. The distribution curve is Gaussian with an average size of 122±4 nm (mean±S.D.). Particle sizing was reproducibly performed at least 3 times.

The present invention provides compositions and methods for inducing immune tolerance toward a protein. This invention is particularly useful in individuals who are on a therapeutic protein therapy and may not have previously exhibited an immune intolerance.

In one embodiment, the present invention comprises administering to an individual a first composition (also referred to herein as a priming composition, which can comprise one or more administrations or doses) comprising a therapeutic protein (such as Factor VIII or any other protein or peptide) complexed with liposomes comprising PS and PC (PS liposomes), or comprising PS, PI and PC and, optionally, cholesterol (PS/PI liposomes). The first administration can be followed up with one or more administrations of the priming composition. The priming compositions can be administered 1 time a week to three times a week. Administration can be carried out for 1, 2, 3, 4, 5 or more weeks. After a suitable period of time allowing immune tolerance to develop (such as at least 4 days after the last primer), the individual can be administered a second composition (one or more administrations) comprising the protein or peptide in the free form, complexed to liposomes or lipidic structures having a different composition than the primary composition, or complexed (covalently or noncovalently) to PEG, or surfactants or microspheres and the like. The lipidic structures (also referred to herein as lipid structures) may include micelles, cochleates, lipidic molecular assemblies and the like. In one embodiment, the individual is administered the second composition (which may be a therapeutic composition) after 4 to 30 days, including all integer number of days and ranges therebetween, of the last priming composition administration. In one embodiment, the individual is administered the second composition after 5, 6, 7, 8, 9, 10, 11, 12, 13, 14 and 15 days of the last of the last priming composition administration. Less immunogenic formulations are disclosed in U.S. Pat. Nos. 7,351,688; 7,875,288; 7,875,289; 7,625,584; 20090053297; PCT/US2010/041196, the relevant disclosure of which is incorporated herein by reference.

This invention can be used for any individual (e.g., a human or a non-human mammal). For example, it can be administered to an individual who has previously been administered the protein or peptide but has not previously developed immune intolerance. The individual may or may not be showing indications of a recent immune intolerance. It is also useful for administration to naïve individuals (i.e., those individuals who have not been administered the protein or peptide previously) Immune intolerance as used herein means the individual should have measurable (by standard methods such as ELISA or activity assays) antibody production. Conversely, a lack of immune intolerance means the individual has no measurable antibodies. By "administered" or "administration" is meant that the protein or peptide is delivered to the individual or introduced into the individual's body by any means or route of delivery.

In one embodiment of the present invention, PS liposomes (30% PS and 70% PC in molar ratio) as well as PI liposomes (50% PI, 50% PC in molar ratio and 5 molar % cholesterol) when complexed with FVIII, showed statistically significant reduction of FVIII immune response in HA mice. PS/PI liposomes (30% PS, 30% PI and 40% PC and, optionally, 5 molar % cholesterol) also showed reduction of immune response. A range of 10% up to 50% molar ratio PS can be used. Thus, the composition of the PS liposomes can be PS:PC at 10:90 to 50:50 and all ranges therebetween. In one embodiment, the composition of PS liposomes is PS:PC at 40:60 to 20:80. In another embodiment the PS liposomes comprise PS:PC at 25:75 to 35:65. For the PS/PI liposomes, the combination of PS and PI is preferably not more than 60 mol % and PC is at least 40 mol %. The PI component of the PS/PI liposomes is from 1 mol % to 30 mol % and all integer mol % values therebetween. For both the PS liposomes and the PS/PI liposomes, the PS should be at least 1 mol %. In one embodiment, PS is at least 10 mol %.

PS, PC and PI may have from 0-20 carbon atoms in the acyl chain. For example, when the carbon atom is 0 for PS, the molecule is O-Phospho-L-Serine (OPLS). In one embodiment, the acyl chains have 1 to 22, 2 to 22, or 6 to 22 carbons (and all integer number of carbons and ranges therebetween). The acyl chains can be saturated or unsaturated. The PC may have one or two acyl chains. For example, the PC may include lysophosphatidylcholine (LPC). For example, in one embodiment, the composition of the PS liposomes was PS:LPC:PC as 30:10:70 mol %. The LPC can be 0 mol % to 20 mol %. In one embodiment, it is 1 mol % to 20 mol % and all integer mol % values and ranges therebetween.

The compositions of the present invention can be delivered by any standard route such as intravenous, intramuscular, intraperitoneal, mucosal, subcutaneous, transdermal, intradermal, oral, and the like. In one embodiment, the priming composition comprising PS or PS/PI liposomes is delivered by the subcutaneous route.

For purposes of this description, protein-PS (such as Factor VIII-PS) means the protein complexed with liposomes comprising PS and PC as described above. While specific description is provided using Factor VIII as an example, it is equally applicable to other proteins.

Liposomes are also referred to herein as lipidic nanoparticles. The phospholipids can be obtained from any available source such as plant or animal. The phospholipids are commercially available or can be synthesized by known methods. For example, PS can be obtained from porcine brain PS or plant-based soy (soya bean) PS.

Similarly, FVIII-PI means Factor VIII complexed with phosphatidylinositol (PI) (such as soy from soya bean) containing liposomes. The composition of these PI liposomes/nanoparticles used was 50% PI, 50% PC in molar ratio and Cholesterol was 5% of total lipid (PI+PC). FVIII-PG means Factor VIII complexed with phosphatidylglycerol (PG) containing liposomes. The composition of these PG liposomes was 30% PG and 70% PC in molar ratio (also denoted as PG30).

The phospholipid composition of the liposomes or lipidic structures in the second composition (which may be a therapeutic composition) may be the same or different from the phospholipid composition of the liposomes of the first composition (which is a priming composition). The phospholipid composition change may include the type of phospholipid or the ratio of different phospholipids. In one embodiment, the therapeutic composition includes LPC and spingosine.

In one embodiment, the frequency of FVIII-PS administration of the priming composition is once-a-week for four weeks via the subcutaneous route. In one embodiment, at least four weekly administrations are used to induce tolerance. More doses of FVIII-PS or FVIII-PS/PI can be used if necessary.

Studies aimed at understanding the underlying mechanism in reduction of antibody response showed that PS, but not charge matched PG, decreased the up-regulation of co-stimulatory signals such as CD40 on dendritic cells. Further, PS also shows increase in the secretion of regulatory cytokine such as TGF-$\beta$. These results indicate that PS reduces antibody response against FVIII possibly by inducing tolerance towards the protein, opening a possibility of tolerance induction therapy as therapeutic utility of lipidic particles.

The results indicate that an inverse/reverse vaccination strategy, in which an individual that is immunologically naïve to a particular protein (e.g., FVIII) or antigen is administered a tolerance-inducing form of said protein (e.g., FVIII-PS) or antigen prior to said individual's exposure to a free, native form of said protein (e.g., FVIII) or antigen, is useful to tolerize the individual to the protein or antigen such that the individual would be immunologically hypo-responsive following subsequent administration of the native form of the protein or antigen. Similar to the current practice of administering "booster" vaccines, this strategy can be repeated in the event said individual becomes immunologically responsive over time following future exposures to said protein or antigen.

Development of immune tolerance against the therapeutic protein can be identified by determining down-regulated expression of co-stimulatory signals on dendritic cells, lowered CD4$^+$ T-cell proliferation, and induced secretion of immuno-regulatory cytokines TGF-$\beta$ and IL-10. One or more of these identifiers can be evaluated in culture conditions. In one embodiment, the development of immune tolerance is specific to the protein against which tolerance is induced (i.e., the protein complexed with the liposomes of the priming composition). By "specific" is meant that an immune response to non-relevant proteins (proteins that were not complexed to the liposomes of the priming composition) is not affected.

In one embodiment, the present invention can be used in individuals with Hemophilia A. A liposomal formulation for FVIII containing both PS, and PS and PI in an attempt to reduce FVIII immunogenicity was developed. The results indicate that PS containing liposomes are useful for reducing immunogenicity of therapeutic proteins and also that such compositions can be delivered by subcutaneous (SC) delivery.

Example 1

Materials: Full length recombinant human FVIII (Baxter Biosciences, Carlsbad, Calif.) was obtained as a gift from the Western New York Hemophilia Foundation. Brain PS, soy-bean derived PI and DMPC were purchased from Avanti Polar Lipids (Alabaster, Ala.). The lipids were dissolved in chloroform, aliquoted to the appropriate concentration, stored at −80° C. and used without additional purification. All solvents and components for the buffers were obtained from Fisher Scientific (Fairlawn, N.J.) or from Sigma (St.

Louis, Mo.) and were used without further purification. Laurdan was purchased from Molecular Probes Inc. (Eugene, Oreg.). Anti-FVIII monoclonal antibodies ESH4, ESH5 and ESH8 were obtained from American Diagnostica Inc. (Greenwich, Conn.) while the antibody N77210M was purchased from Biodesign International (Saco, Me.). Goat anti-mouse Ig and rabbit anti-rat Ig conjugated to alkaline phosphatase were purchased from Southern Biotechnology Associates, Inc. (Birmingham, Ala.). Normal human plasma and FVIII-deficient human plasma were obtained from Trinity Biotech (County Wicklow, Ireland). Bovine serum albumin (BSA) was purchased from Sigma (St. Louis, Mo.) while the phosphatase substrate system (diethanolamine buffer and p-nitrophenyl phosphate) was purchased from KPL Inc. (Gaithersburg, Md.). DiaPharma Group (West Chester, Ohio) provided the Coamatic FVIII kit for the detection of FVIII in plasma.

Preparation of Small Unilamellar Vesicles (SUVs): Brain PS (transition temperature $T_c$~6-8° C.), soy-bean derived PI and DMPC ($T_c$~23° C.) were used in the liposomes. Small unilamellar liposomes were prepared by dry lipid-film hydration method followed by multiple extrusions. Required aliquots of PS, PI and DMPC in chloroform were taken in a Kimax glass tube in the molar ratio of 30:30:40 respectively. The mixture was vortexed and the chloroform evaporated under nitrogen gas using Buchi rotaevaporator (Buchi R-200, Fischer Scientific, N.J.) to form a thin film of lipid. This film was rehydrated with $Ca^{+2}$ free Tris buffer (300 mM NaCl, 25 mM Tris, pH 7.0 prepared in sterile, pyrogen free water for injection), vortexed and incubated at 37° C. for 3 minutes. This formed multilamellar vesicles (MLVs), which then were extruded multiple times through double-stacked polycarbonate membranes (GE Osmonics Labstore, Minnetonka, Minn.) with pore size 80 nm. The extrusion was done with a high pressure extruder (Lipex Biomembranes Inc., Vancouver, Canada) using nitrogen gas, keeping the pressure at ~200 psi. SUVs were produced by extrusion, and the preparation was sterilized by filtering it through a sterile 0.22 um Millex™-GP filter unit (Millipore Corporation, Bedford, Mass.).

Lipid Recovery: The phosphate recovery and phospholipid concentration of the liposomes were measured by inorganic phosphorus assay, as described by Bartlett[30]. Briefly, the liposome samples were prepared in triplicates in glass test tubes. Distilled water was used as a blank solution where as standard phosphate solution (20 μgmL) was used for standard curve. Standard curve was prepared using 1 μg to 3 μg phosphate/ml. The blocks were heated up to 200° C. 400 μL of 10 $NH_2SO_4$ was added in each tube and allowed to digest for 1 h. Tubes were then allowed to cool and 100 μL of 30% hydrogen peroxide ($H_2O_2$) was added to each tube, mixed and allowed to digest for 1.5 h. Then 4.6 mL of molybdate reagent was added in each tube, mixed and further 100 μL of ascorbic acid was added. After ascorbic acid was added, tubes were heated for 10 min in boiling water. Tubes were then allowed to cooldown to room temperature and absorbance was measured at 830 nm Phosphate concentrations from liposomes were estimated using the standard curve. The results were expressed as μmoles of phospholipid/ml and exact amount of phospholipids were then used to titrate the dose of lipid for FVIII incorporation.

Association of Protein with Liposomes: FVIII was associated with the liposomes at a protein-to-lipid ratio of 1:10,000 at all times unless otherwise mentioned. Required amounts of the liposome preparation, FVIII and Tris buffer were mixed gently with a pipette under sterile conditions and incubated at 37° C. for 30 minutes. The liposomes were used immediately after association or stored at 4° C. and used within 24 h. In order to investigate the effects of $Ca^{+2}$ on FVIII association efficiency, liposomes were prepared as described above, but with Tris buffer containing 5 mM, 0.5 mM, 0.1 mM or 0 mM $Ca^{+2}$.

Particle Size measurement: The particle size was measured by a dynamic light scattering Nicomp Model CW 380 size analyzer (Particle Sizing Systems, Santa Barbara, Calif.) as described by Purohit et al. A small amount of the preparation was diluted in Tris buffer and the size was measured both before and after association with FVIII. An intensity-weighted Gaussian curve was used to determine particle size distribution.

Separation of particle-associated FVIII from free FVIII: To measure the amount of FVIII associated with the liposomes, discontinuous dextran density gradient ultracentrifugation was performed as described previously. Liposomes (0.5 mL) were mixed with 1 mL of 20% w/v dextran in a 5 mL polypropylene tube. 3 mL of 10% w/v dextran was added slowly, taking care to form two distinct layers without mixing. Finally, 0.5 mL of Tris buffer (0% dextran) was added to the surface of the 10% w/v dextran layer, thus forming three distinct layers with gradient densities. This tube was ultra-centrifuged at 45,000 rpm for 30 minutes, at the end of which most of the liposome-bound FVIII collected in the topmost layer while a small amount collected in the middle layer; the free FVIII collected at the bottom of the tube. The three layers were separated by pipetting and FVIII activity was measured in each layer by the activated partial thromboplastin time (aPTT) assay.

Association Efficiency Studies: The aPTT assay was performed using a COAG-A-MATE coagulometer (Organon Teknika Corporation, Durham, N.C.) as described by Over. After the dextran density gradient ultracentrifugation (Dextran MW 35000-45000), association efficiency was calculated by measuring amount of protein in the top layer using activity, spectroscopic and protein quantitation assays. Briefly, the activity assay was performed by appropriate dilutions of each separated layer in imidazole buffer. Then 100 μL of the diluted samples were mixed with 100 μL of FVIII-deficient human plasma. After warming the mixture, 100 μL of the activator (platelin-L reagent) was added. Upon activation, 100 μL of $CaCl_2$ was added. The activator and $CaCl_2$ facilitate clot formation and the clotting time was measured for each diluted sample. The aPTT assay was also performed on known concentrations of standard FVIII. A semi logarithmic standard curve of activity vs. clotting time was plotted. The clotting time obtained for each separated layer of the liposomes was then correlated with FVIII activity by linear regression from the standard curve.

Protein Conformation Studies: The tertiary structure of FVIII after association with the particles was monitored using fluorescence spectroscopy. The intrinsic fluorescence of tryptophan (Trp) residues in FVIII was utilized to obtain fluorescence spectra (assuming that all Trp residues contribute equally to the spectra). SUVs were prepared as described above and FVIII was associated with the particles, keeping the concentration of FVIII at 5 ug/mL in Tris buffer. The protein-to-lipid ratio was kept at 1:2500. An I-shaped cuvette with two path lengths (0.4 cm towards the emission path and 1 cm towards the excitation path) was used to minimize the inner filter effect. Using a PTI-Quantamaster fluorescence spectrophotometer (Photon Technology International, Lawrenceville, N.J.) equipped with a xenon arc lamp and a Peltier unit, an emission scan was acquired over the wavelength range 300-400 nm. The excitation wavelength was kept at 265 nm to remove interference due to Raman band at 310 nm; the slit width for the excitation and for the emission paths was set at 4 nm. Spectra were acquired at 25° C. for the membrane-bound FVIII as well as for the vesicles alone, and their difference was used to obtain spectra for FVIII. This, along with the use of a long pass filter, corrected the contribution of the vesicles towards the FVIII spectra.

Sandwich ELISA (enzyme-linked immuno-sorbent assay): To test the hypothesis that the liposome could be shielding antigenic epitope(s) of FVIII, a sandwich ELISA was performed as described previously. Briefly, Nunc-Maxisorb 96-well plates were coated overnight at 4° C. with 50 µL/well of capture antibodies (ESH4, ESH5, ESH8 and N77210M) at a concentration of 5 µg/mL in carbonate buffer (0.2 M, pH 9.6). The next day, 200 µL/well of blocking buffer (1% Bovine serum albumin (BSA) in PBS) was used to block the wells and the plates were incubated for 2 h. Next, 0.5 ug/mL dilutions of free FVIII, liposomal FVIII and blank liposomes were prepared. The liposomal preparations were diluted to 1:5000, 1:10,000 and 1:50,000 in blocking buffer. The plates were incubated with the samples at 37° C. for 1 h after which 100 uL/well of rat polyclonal antibody (1:500 dilution in blocking buffer) was added. After incubation for an hour at room temperature, 100 µL/well of detection antibody (1:1000 dilution of goat anti-rat IgG-alkaline phosphatase conjugate in blocking buffer) was added and incubated for 1 h at room temperature. 200 µL/well of 1 mg/mL p-nitrophenyl phosphate in diethanolamine buffer was then added and incubated at room temperature for 30 min 100 µL/well of 3 N NaOH was added to quench the reaction and the absorbance was measured at 405 nm. At each step except quenching, the plates were washed 6 times with 100 µL/well of PBT (2.7 mM KCl, 140 mM NaCl, 1.8 mM $KH_2PO_4$, 10 mM $Na_2HPO_4.2H_2O$, 0.05% w/v Tween-20).

Laurdan Fluorescence: In order to investigate liposome stability and to study the membrane dynamics of PS, PI and DMPC within the particles, laurdan (6-dodecanoyl-2-dimethylamino naphthalene) fluorescence was performed. Laurdan has been established as a sensitive probe to investigate lipid membrane phase properties. It partitions between the hydrophobic and hydrophilic domains of lipids and has different emission wavelengths depending on its environment.

MLVs for four different liposomes-100% DMPC, 70% DMPC: 30% PS, 70% DMPC: 30% PI and 30% PS: 30% PI: 40% DMPC—were prepared, as described in section 2.2. Laurdan was added to the lipid mixture in the ratio 1:1000 (laurdan:lipid) before thin-film formation. 0.5 mM of the vesicles was taken in an I-shaped cuvette with two pathlengths (0.4 cm towards the emission path and 1 cm towards the excitation path). Fluorescence emission spectra were acquired for each liposomal preparation by exciting the samples at 340 nm and monitoring emission over 425-550 nm Excitation spectra were also acquired by exciting the samples between 320-420 nm and measuring emission at 440 nm and at 490 nm. Further, a temperature scan was performed over 15-30° C. for each liposomal preparation to study their phase transition properties. The excitation generalized polarization ($GP_{Ex}$) was obtained at 340 nm and at 410 nm and was defined as: $(I_{440}-I_{490})/(I_{440}+I_{490})$, where $I_{440}$ and $I_{490}$ denote the fluorescence intensities at the blue edge (440 nm) and at the red edge (490 nm) of the spectrum respectively.

Immunogenicity studies: FVIII-knockout mice (8-12 weeks old) of the C57BL/6J strain were used. These mice have a target deletion in exon 16 which causes a disruption in the production of active FVIII. Although murine hemophilia A is phenotypically less severe than in humans, it provides an adequate model for qualitative comparison of relative immunogenicity. Sex does not impact immunogenicity in this model, therefore male mice as well as female mice were used in the immunogenicity studies.

All animal studies were authorized and performed according to the guidelines set by the Institutional Animal Care and Use Committee (IACUC) of the University at Buffalo. When necessary, they were sacrificed by exsanguination under isoflurane anesthesia. A Limulus amebocyte lysate test (Charles River Laboratories, Inc., Wilmington, Mass.) was performed on the liposomes before in vivo administration to test for the presence of endotoxins. Detection limit of the limulus amoebocyte assay is 0.001 EU/mL. Formulations lower than the detection limits were considered to be free from any endotoxins. These Endotoxin-free preparations were administered intravenously as well as subcutaneously in hemophilic mice.

For the immunogenicity studies, male mice (n=7) were injected with 400 IU/kg of either free FVIII or the liposomal formulation by IV injections. Similarly, female mice (n=9) were injected subcutaneously with the same dose under the dorsal skin fold. The injections were given once a week, for four weeks followed by a washout period of two weeks. Six weeks after the first injection, the mice were sacrificed and blood was collected via cardiac puncture. The two week washout period is sufficient to avoid any interference from circulating FVIII. This is based on our PK studies that show that the half life of FVIII in this animal is about 2.5 h for (IV) and about 8 h following SC administration. The blood was mixed in a 10:1 (v/v) ratio with acid citrate dextrose (ACD) buffer containing 85 mM sodium citrate, 110 mM D-glucose and 71 mM citric acid. This mixture was centrifuged immediately at 5000 g for 5 min at 4° C. to obtain plasma which was stored at −80° C. until further analysis.

Total FVIII-specific antibody titers for IV and SC routes were measured by an antibody capture ELISA. Briefly, Nunc-Maxisorb 96-well plates were coated with 50 µL/well of 2.5 µg/mL FVIII in sodium carbonate buffer (0.2 M, pH 9.6) and allowed to stand overnight at 4° C. The next day, 200 µL/well of blocking buffer (1% BSA in PB) was used to block the wells and the plates were incubated for 2 h. Dilutions of plasma samples and of the standard antibody (ESH8) were made in blocking buffer and 50 µL/well of the samples was added. The plates were incubated with the samples at 37° C. for 1 h. Next, 50 µL/well of detection antibody (1:5000 dilution of goat anti-mouse IgG-alkaline phosphatase conjugate in blocking buffer) was added and incubated for 1 h at room temperature. 100 µL/well of 1 mg/mL p-nitrophenyl phosphate in diethanolamine buffer was then added and incubated at room temperature for 30 min. 100 µL/well of 3 N NaOH was added to quench the reaction and the absorbance was read at 405 nm. The plates were washed 6 times before each step (except quenching) with 100 µL/well of PBT (2.7 mM KCl, 140 mM NaCl, 1.8 mM $KH_2PO_4$, mM $Na_2HPO_4.2H_2O$, 0.05% w/v Tween-20). In order to ensure minimum plate-to-plate variability, a parameter known as Plate Specific Factor (PSF) was calculated for each plate as described earlier.

Neutralizing antibody titers were measured by Nijmegen-modified Bethesda assay. Briefly, several dilutions of plasma samples were made in FVIII-deficient human plasma. 200 µL of normal human plasma was mixed with 200 µL of the diluted plasma samples and incubated for 2 h at 37° C. Following incubation, 200 µL of each sample was taken and the clotting time was measured using aPTT assay. A standard curve was generated by performing the assay on samples containing a known concentration of FVIII. Using the standard curve, 50% inhibition of FVIII activity was calculated for the samples. The neutralizing antibody titer was expressed in terms of Bethesda Units (BU). 1 BU is defined as the antibody titer that produces 50% inhibition of coagulant activity when 1 mL of plasma is incubated at 37° C. for 2 h.

Statistical Analysis: Student's t-test, Mann-Whitney, non-parametric test and one-way ANOVA were performed using Minitab (Minitab Inc., State College, Pa.) to obtain p values for statistical comparison.

Results:

Liposomes containing PS, PI and DMPC were prepared and associated with FVIII by triggered loading, as described in the experimental procedures section. The liposomes were subjected to dextran density gradient ultracentrifugation to separate free protein from liposome-associated protein. The amount of FVIII in each layer of the dextran gradient was quantified using the aPTT assay to obtain % association efficiency. The association efficiency for the liposomes in $Ca^{+2}$ containing buffer was low (<50%, data not shown). $Ca^{+2}$ is known to have high affinity for PS and is required for proper orientation and biological activity of PS. However, $Ca^{+2}$ is also implicated in membrane fusion of PS vesicles. The chelation of $Ca^{+2}$ by the negatively-charged head group of PS may lead to the formation of a large fused vesicle which may not bind to FVIII efficiently, hence the low association efficiency observed with $Ca^{+2}$ containing buffer.

Conversely, about 77±7% (mean±S.D., n=3) of FVIII was associated with the liposomes dispersed in $Ca^{+2}$-free buffer. Therefore PS/PI/DMPC liposomes in $Ca^{+2}$ free buffer were selected for all further experiments. The particle size distribution was normal, with a Chi-squared value of ≤1.0 which indicated that Gaussian analysis gave the best possible fit (FIG. 1). The average particle size was about 122±4 nm (mean±S.D.). There was no significant difference in particle size before and after association of FVIII, indicating that there was no vesicle aggregation or fusion following the addition of FVIII to the liposomes.

Figure 2:
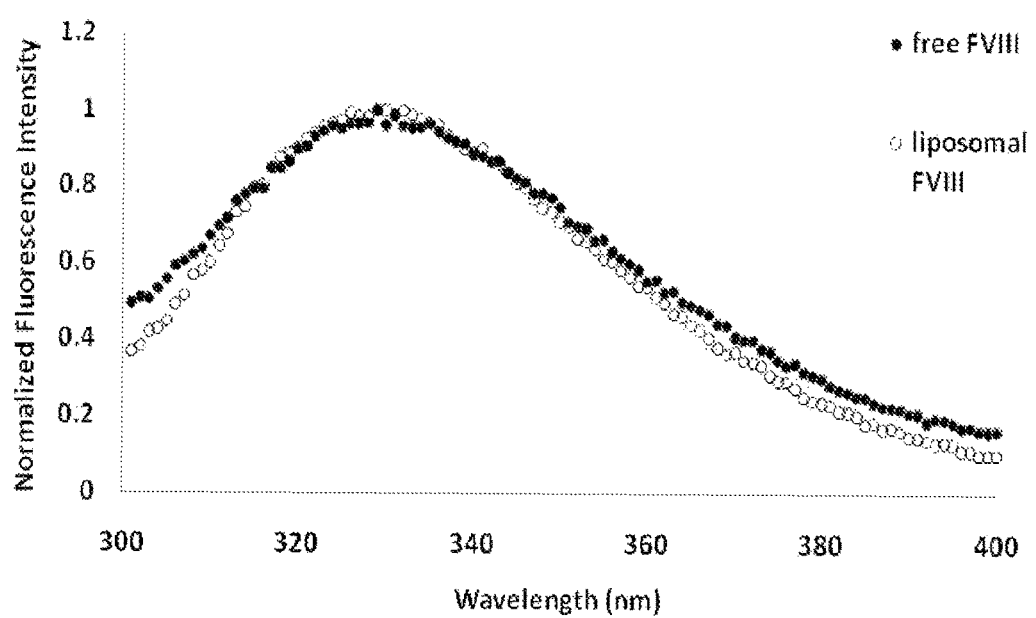
FIG. 2: Fluorescence study to monitor tertiary structural conformation of liposome FVIII. Fluorescence emission spectra were acquired 3 times reproducibly for free FVIII (filled symbols) and for FVIII-PS/PI liposomes (empty symbols). The figure represents normalized fluorescence intensities of the two formulations.

Conformational Studies: The tertiary structure of a protein is greatly responsible for its activity, making it crucial to ensure protein conformational integrity. Fluorescence spectroscopy was used to acquire an emission scan of FVIII before and after association with liposomes. FVIII has 36 Trp residues (22 in the heavy chain, 14 in the light chain) and the intrinsic fluorescence of these Trp residues was used to obtain the spectra. The free FVIII spectrum showed a peak at about 333 nm. There was no significant change in the FVIII spectrum after association with the liposome (FIG. 2). The lack of spectral changes indicates that the tertiary conformation of FVIII was preserved after incorporation into liposomes. Furthermore, association of FVIII with liposomes did not result in a major blue shift, which suggests that a greater part of FVIII exists in a hydrophilic environment. If FVIII were intercalated in the lipid membrane, there would be a substantial shift towards shorter wavelength and an increase in fluorescence intensity. Therefore, the spectral data suggests that FVIII is either encapsulated within the aqueous core of the liposome or bound to the external surface of the bilayer.

Sandwich ELISA: In order to further investigate the topology of FVIII associated with liposomes, a sandwich ELISA was performed. Four monoclonal antibodies ESH4, ESH5, ESH8 and N77210M, directed against the C2 domain (residues 2302-2332), a1 acidic region, C2 domain (residues 2248-2285) and A2 domain respectively were used to test which epitopes of FVIII, if any, are shielded by the lipids. The principle behind this assay lies in competitive binding between lipid and antibody for FVIII epitopes. Luminal location of the protein is expected to show a reduction in binding of all the monoclonal antibodies used in this study, and will be monitored by a decrease in optical density with an increase in lipid concentration. Alternatively for surface-bound protein, only part of the protein is shielded and would show reduction in binding only to the antibodies that recognize the shielded epitopes. Free FVIII-antibody binding was considered to be 100% and was used to normalize the binding % for the liposomes. Blank liposomes used as controls did not show any lipid concentration-dependent changes in optical density with an increase in lipid concentration from 0 µM to 178 µM. This indicates lack of non-specific binding of liposomes to the antibodies.

Figure 3:
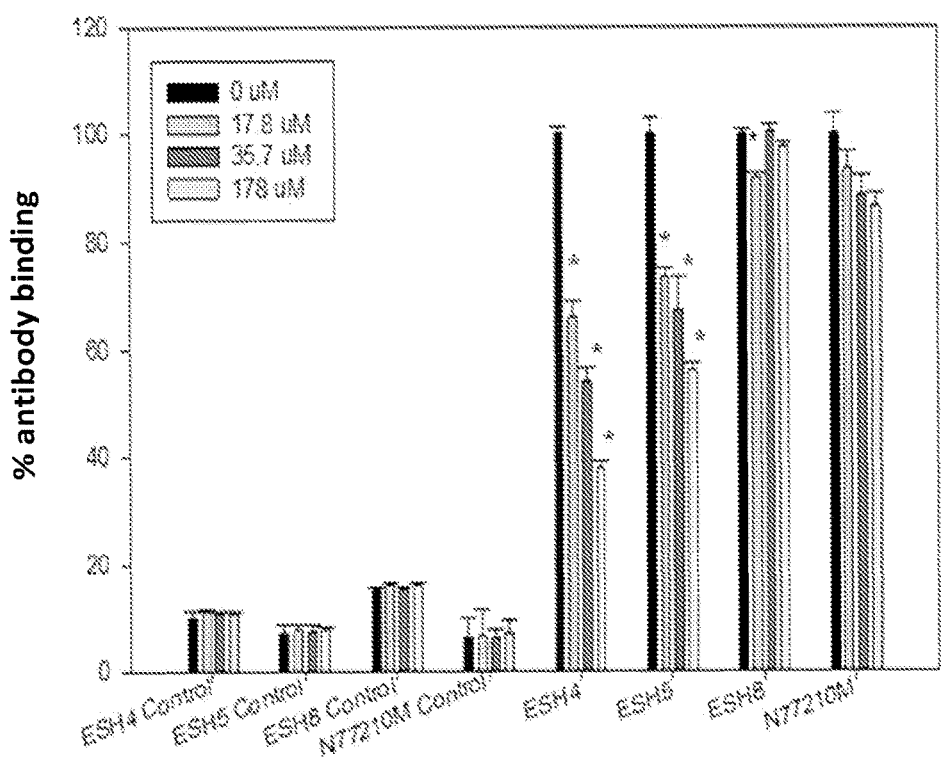
FIG. 3: Representative plot of Sandwich ELISA to study epitope mapping of liposomal FVIII using monoclonal antibodies ESH4, ESH5, ESH8 and N77210M. The lipid concentrations used were 0 uM, 17.8 uM, 35.7 uM and 178 uM. Blank liposomes were used as controls. The data was analyzed using a one-way ANOVA (*p<0.01). The data were acquired reproducibly 3 times.

In case of ESH4 and ESH5, lipid concentration-dependent decrease in antibody binding was observed (FIG. 3). As the lipid concentration was increased from 17.8 µM to 178 µM, the optical density reduced significantly. This suggests that the particle may shield epitopes within the C2 domain and the a1 acidic region. The data also agree with previous results concerning the protective effect of PS on the C2 domain (2303-2332 residues). There was no significant difference for epitopes within the heavy chain and the 2248-2285 residues in the light chain, indicating that the lipid particle may not completely shield these FVIII epitopes. This is consistent with no shift in fluorescence peak maxima for FVIII associated with PS/PI/DMPC liposomes (FIG. 2). However, lipid particles containing PI and DMPC shielded substantial surface area of the protein because of packing defects caused by PI in DMPC bilayer allowing deeper penetration of the protein. This topology was consistent with the fluorescence spectra that showed blue shift for FVIII associated with PI/DMPC particles.

Laurdan Fluorescence: Lipid lamellarity and miscibility are critical for the stability of liposomes. The phase behavior of PS and PI are known individually; however their combined effect on DMPC bilayer is not known. Phase separation of PS and PI from PS/PI/DMPC vesicles could lead to instability of liposomes. In order to investigate the stability and membrane dynamics of PS and PI in DMPC liposomes, laurdan was used as a fluorescent probe. The lauric acid chain of laurdan is located in the hydrophobic region of phospholipids while the fluorescent moiety localizes in the hydrophilic region of phospholipids. Any dipolar relaxation caused by transition from gel to liquid crystalline state results in a spectral red shift from 440 nm to 490 nm. This makes laurdan very sensitive to changes in the polarity and lamellarity of its environment. Laurdan fluorescence provides a useful parameter, $GP_{Ex}$ which can be used to quantify the gel and liquid crystalline phases of phospholipids. $GP_{Ex}$ is a function of solvent polarity and viscosity, with $GP_{Ex}$ values decreasing as the polarity of its environment increases.

Figure 4A:
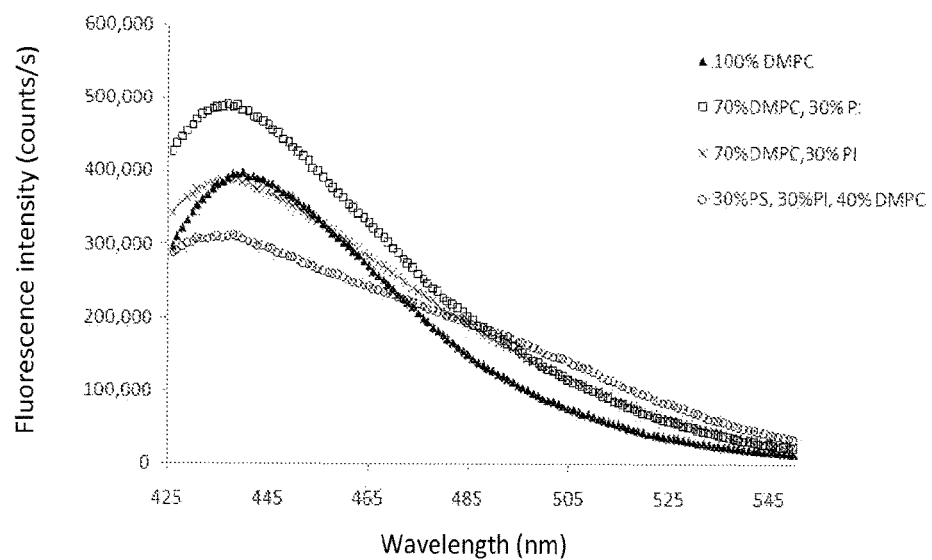
FIG. 4: Liposomal stability studies using Laurdan as a fluorescent probe (a) at 15° C. and (b) at 30° C. Emission spectra were obtained reproducibly (n=3) for liposomes made of 100% DMPC, 70% DMPC: 30% PS, 70% DMPC: 30% PI and 30% PS: 30% PI: 40% DMPC. The samples were excited at 340 nm and emission was monitored over 425-550 nm. The data shows that the liposomal particles are stable.
FIG. 4(c): Membrane dynamics studies using Laurdan as a fluorescent probe. Excitation GP at 340 nm was obtained from 15-30° C. for liposomes made of 100% DMPC, 70% DMPC: 30% PS, 70% DMPC: 30% PI and 30% PS: 30% PI: 40% DMPC. The data was obtained reproducibly (n=3); this is a representative plot.
Figure 4B:
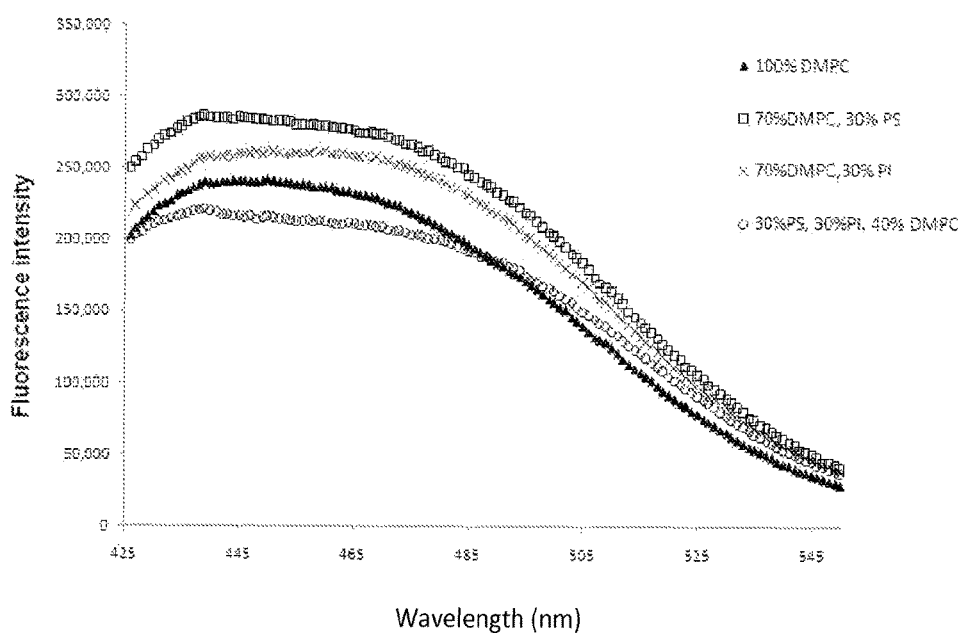

In order to investigate lipid miscibility and the effect of PS and PI on DMPC bilayer properties, emission scans were acquired for liposomes made of 100% DMPC, 70% DMPC: 30% PS, 70% DMPC: 30% PI and 30% PS: 30% PI: 40% DMPC. FIGS. 4a and 4b show that fluorescence intensity decreased as a function of temperature, accompanied by a gradual red shift. This red shift is a typical property of laurdan as its environment changes from a rigid gel state to a polar liquid crystalline state due to increase in water penetration. At 15° C., pure DMPC vesicles display a distinct emission peak at 440 nm, consistent with the emission maximum of laurdan in the gel state (FIG. 4a). The peak shifted perceptibly at 30° C., indicating a phase transition. However, upon addition of PS and PI, this temperature-dependent spectral shift was minimal. The spectral characteristics resembled that of fluid phase even at 15° C. (FIG. 4a, open circles), suggesting that the presence of anionic lipids together fluidizes the DMPC membrane and shows liquid crystalline characteristics.

Figure 4C:
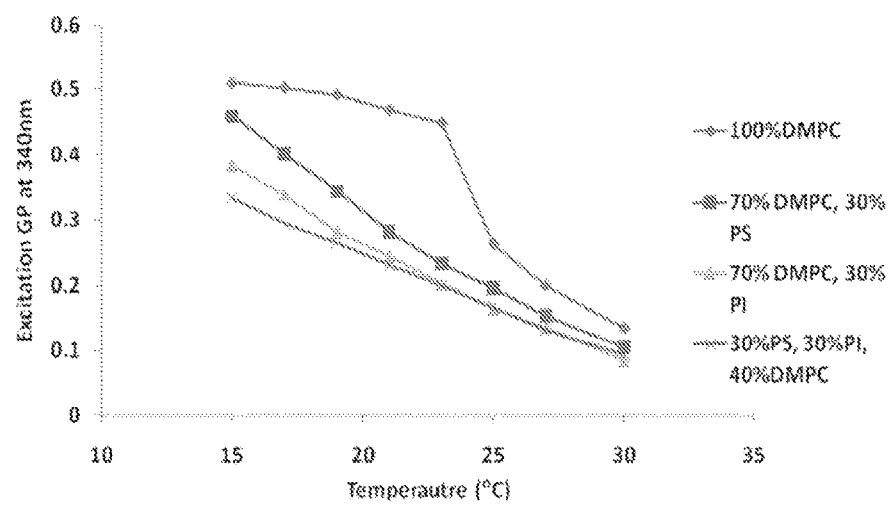
Figure 4C:
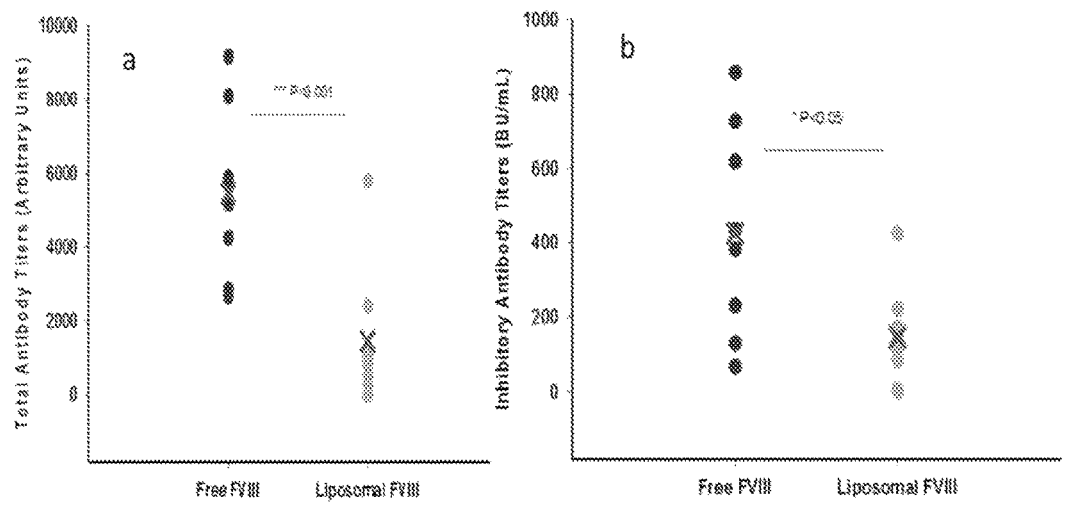

The $GP_{Ex}$ value for pure DMPC vesicles at 15° C. is ~0.5 (FIG. 4c). Addition of PS into DMPC vesicles resulted in lowering of the $GP_{Ex}$ in the gel phase; this drop in $GP_{Ex}$ was more pronounced in the PI/DMPC liposomes. This is suggestive of an alteration in the lamellarity of the membrane, with laurdan detecting fluid domains in the presence of PS or PI. Interestingly, combining PS and PI within the DMPC vesicle led to a further decrease in $GP_{Ex}$. This lowering of $GP_{Ex}$ is most likely the result of the combined effects of PS and PI and cannot be obtained by PS/DMPC or PI/DMPC alone, indicating that PS and PI may work in concert to disrupt the compact packing of DMPC molecules, resulting in a more fluid liposome with a low $T_c$. Further, the phase transition profile for the 100% DMPC liposomes obtained over a range of 15-30° C. showed a sharp transition at ~23° C., while no clear $T_c$ could be identified from the transition profiles of the other liposomes (FIG. 4c), indicating that the addition of PS, PI and both anionic lipids together abolished the transition.

Immunogenicity studies: Immunogenicity of FVIII represents most serious complication to the current hemophilic therapy and dramatically increases the cost of the treatment. Antibodies generated against FVIII can neutralize its biological activity, while other antibodies form a complex with FVIII and accelerate its clearance. Most neutralizing antibodies are generated against the A2, A3 and C2 domain of FVIII. Therefore incorporating FVIII into liposomes may shield its epitopes and prevent interaction with antibodies. Since the sandwich ELISA demonstrated shielding of epitopes within the C2 domain and the a1 region, in vivo immunogenicity studies were carried out to test the immunomodulatory properties of the liposome.

Figure 5C:
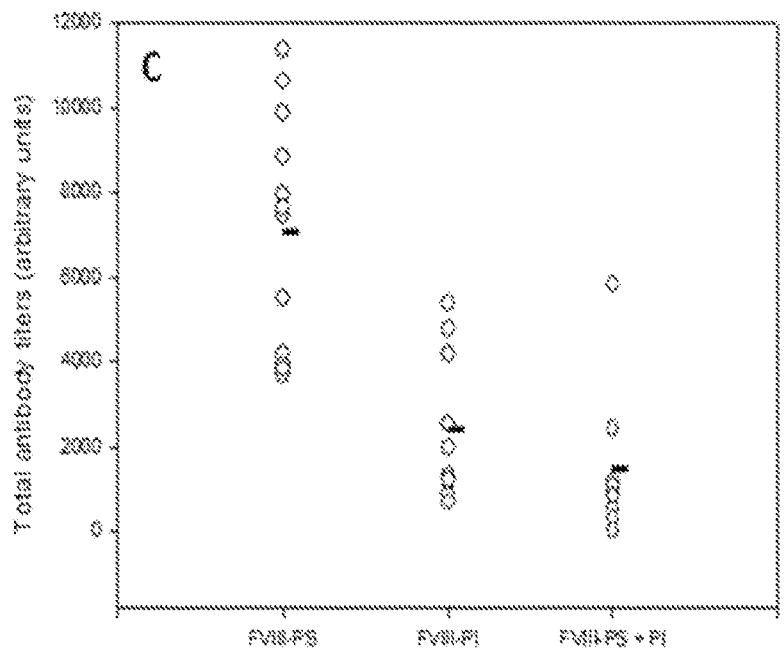
FIG. 5: Effect of PS and/or PI liposomal FVIII on immunogenicity of FVIII after SC administration. a) The mean of total antibody titers (cross) and individual (closed circles) antibody titers against FVIII as determined by antibody capture ELISA in HA mice immunized via S.C. administration of free FVIII, liposomal FVIII. (***P<0.001, non-parametric Man-Whitney Test) b) The mean of inhibitory titers (cross) and individual (closed circles) antibody titers against FVIII and liposomal FVIII as determined by the Nijmegen modification of the Bethesda assay in HA mice immunized via S.C. administration of free FVIII, liposomal FVIII. (*P<0.05, non-parametric Man-Whitney Test). Panels (c) and (d) show a comparison of total and neutralizing antibody titers respectively generated by FVIII-PS liposomes, FVIII-PI liposomes and FVIII-PS+PI liposomes (PS:PI:PC 30:30:40 and 5% cholesterol).
Figure 5D:
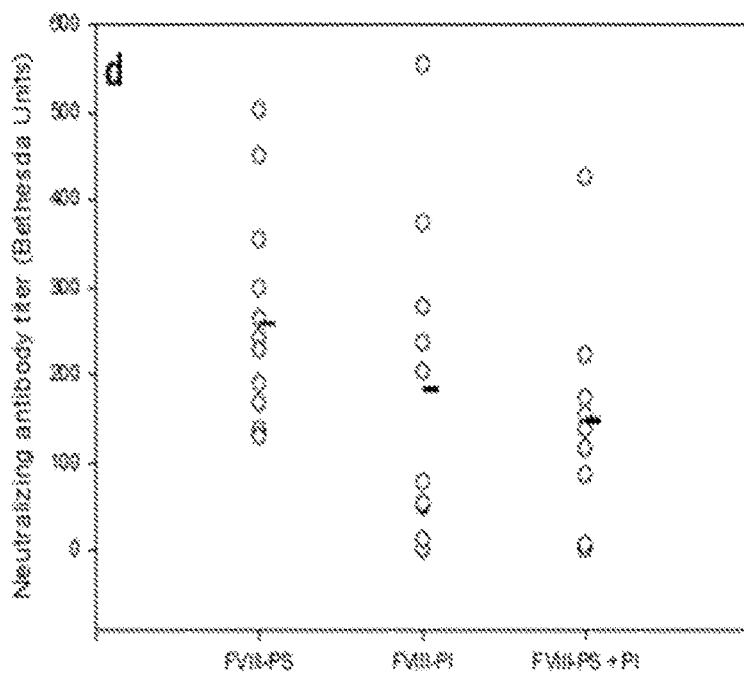

A murine hemophilia A model was used to test the relative immunogenicity of liposomal FVIII against free FVIII. Since the pattern of immune response is qualitatively similar to that in hemophilic humans, this model is quite useful and has been used to measure relative immunogenicity of FVIII. Naïve hemophilic mice were administered 400 IU/kg of free FVIII or liposomal FVIII via IV and SC route for 4 weeks. Total FVIII-specific antibody titers for IV and SC routes were measured at the end of six weeks by an antibody capture ELISA. Neutralizing antibodies were measured using the clinically-accepted Nijmegen-modified Bethesda assay. The mean neutralizing antibody titer was comparable in case of animals injected with liposomal FVIII intravenously [503±48 (S.E., n=7) vs. 529±73 S.E., n=7] compared to free FVIII. However, administration of SC liposomal FVIII produced significantly lower mean total antibody titers 1453±619 (S.E., n=9) when compared to the groups of mice which received free FVIII 5469±827, (S.E., n=9,) (FIG. 5a). Similarly for the groups of mice which received liposomal FVIII by SC route the mean inhibitory antibody titers were significantly lower (Mann-Whitney, nonparametric test, P<0.005) 146±42 (S.E., n=9,) than the groups of mice which received free FVIII 425±74 (S.E., n=9,) (FIG. 5b). Further, from FIGS. 5c and 5d it is clear that presence of both PS and PI within the same particle, is superior in reducing the immunogenicity compared to PS alone or PI alone particles. For PS alone treatment group, the total titers were observed to be 7057±807 (n=12) and for PI alone treatment group the observed titers were 2379±556 (n=10) but the animals that received both PS and PI elicited significantly lower antibody response of 1454±318 (n=9). Similar observations were made for inhibitory titers following the administration of PS and PI particles. Together, these results suggest that PS/PI containing liposomes reduce FVIII immunogenicity in vivo.

The development of neutralizing anti-FVIII antibodies is an unresolved problem that has complicated hemophilia A treatment for years. Strategies such as immune tolerance induction require very high doses of FVIII, which make the treatment expensive, besides proving ineffective over a long time. Most neutralizing antibodies are directed against the light chain of FVIII. Interestingly, the epitopes in the C2 domain form a binding site for phospholipids. Therefore, formulating FVIII in a liposome to shield epitopes within the C2 domain is likely to overcome antibody formation.

Liposomes containing PS, PI and DMPC in the molar ratio 30:30:40 were developed and about 77% FVIII was associated with the particles. Biophysical characterization of the particles using laurdan fluorescence showed that PS and PI form stable, fluid liposomes with DMPC. Fluorescence spectroscopy showed a lack of significant spectral changes after association of FVIII with the liposomes, indicating that the tertiary structure of FVIII was not altered after interaction with the liposome (FIG. 2). The absence of a discernible blue shift suggests that a significant part of the FVIII molecule is exposed to the external milieu, with the C2 domain involved in lipid binding. This is consistent with the sandwich ELISA study that implicates shielding of a part of the C2 domain. SC immunogenicity studies in hemophilia A mice revealed that the liposomes significantly reduced the antibody response against FVIII.

The low immunogenicity may be attributed to the protective influence of the liposome that shields immunodominant epitopes in the C2 domain and the a1 acidic region. The drastic decrease in FVIII immunogenicity following SC administration suggests feasibility of SC administration that PS/PI containing liposomes may help overcome the long-standing impediment of highly immunogenic SC delivery of proteins. SC route of administration offers several advantages with regard to FVIII delivery. Along with increased patients' ease of administration, it could serve to prolong FVIII circulation. Prolonged circulation time may potentially reduce the frequency of protein administration as well as related immunogenicity and cost of therapy. In addition to shielding of immunodominant epitopes, the immunomodulatory properties of PS and PI are likely to play a significant role in reduction of FVIII immunogenicity. The data also shows that presence of both PS and PI within the same particle reduces antibody response to a greater extent compared to particles containing PS or PI alone (FIG. 5). While not intending to be bound by any particular theory, it is considered that the combined immunomodulatory effects of these two anionic lipids could contribute to this reduction.

The interaction of PS and PI with dendritic cells (DCs) present in the SC region may play a significant role in modulating immune response. DCs are a class of antigen presenting cells (APCs) implicated in priming T-cells during an immune response. Upon maturation, they process antigens and stimulate T-helper cell ($T_H$ cell) proliferation by upregulating costimulatory signals like CD40 and CD86. DCs are believed to endocytose FVIII by binding to FVIII mannose ligands via mannose receptors. PS- and PI-containing liposomes for FVIII reduce costimulatory signals to $T_H$ cells, resulting in low titer levels. Cell-culture studies involving exposure of DCs to FVIII-PI and FVIII-PS showed increased secretion of regulatory cytokines TGF-β1 and IL-10 along with decreased expression of costimulatory signals like CD40 and CD86 and pro-inflammatory cytokines IL-6 and IL-17. This is characteristic of tolerogenic DCs. SC administration of FVIII-liposomes may potentially lead to interaction of PS/PI with immature DCs, upregulation of TGF-β1 and polarization of naïve $T_H$ cells into regulatory T cells ($T_{reg}$ cells). This may cause modification of immune response and result in generation of tolerance towards FVIII.

Further, the presence of PS and PI together within the same liposome could also help to overcome another impediment in SC delivery of proteins, namely incomplete bioavailability. FVIII is a 280 KDa macromolecule containing 2332 amino acids and cannot easily cross capillary fenestrae from SC tissues. However, the SC region is rich in lymphatic vessels, and several proteins as well as liposomes have been shown to enter the systemic circulation via the lymphatics. PS-containing liposomes have a great propensity to be taken up by the lymphatics. Indeed, previous preliminary pharmacokinetic data indicate that SC administration of PS-containing FVIII liposomes improved protein bioavailability. During lymphatic transport, liposomes encounter macrophages and subsequent phagocytosis triggers increased antigen uptake by macrophages, resulting in to limited bioavailability. Regardless of the avidity of PS for lymphatic uptake, bioavailability could be improved by reducing uptake of PS-containing liposomes by macrophages. A popular approach to reduce interaction of liposomes with macrophages is by PEGylation, in which liposomes are modified using various polyethylene glycol (PEG) derivatives. Although this method confers stealth properties on the liposome, it also increases liposome size. Large particles are likely to remain at the site of injection rather than migrating into the lymphatics, making PEGylation a questionable approach for SC delivery. The use of PI as a stealth lipid could provide a feasible alternative to PEGylation, since it resists RES uptake without increasing particle size. PI liposomes have shown prolonged systemic circulation. PI containing liposomes are known to suppress phagocytosis by macrophages. Although the exact mechanism behind this is not known, it is believed that the multiple —OH groups of PI interact with water molecules, shielding the negative charge of its head group and making it highly hydrophilic. The increased surface area causes steric hindrance which prevents interaction with opsonins, thus resisting RES uptake by macrophages. These stealth properties of PI, coupled with avid lymphatic uptake of PS, could greatly increase the bioavailability of FVIII. Irrespective of the bioavailability, use of immunomodulatory lipids PS and PI can induce tolerance to FVIII to improve safety and efficacy of FVIII.

The results obtained indicate that PS and PI containing liposomes could serve as an effective means to deliver FVIII subcutaneously to reduce its immunogenicity and to induce tolerance in hemophilia A therapy.

Example 2

ACD, acid citrate dextrose; APC, antigen presenting cell; aPTT, activated partial thromboplastin time; BSA, bovine serum albumin; DC, dendritic cell; DMPC, dimyristoyl phosphatidylcholine; ELISA, enzyme-linked immunosorbent assay; FVIII, factor VIII; $GP_{Ex}$, excitation generalized polarization; IV, intravenous; MLVs, multilamellar vesicles; PB, phosphate buffer; PBT, Tween 20 containing phosphate buffer; PEG, polyethylene glycol; PI, phosphatidylinositol; PS, phosphatidylserine; PSF, plate specific factor; RES, reticuloendothelial system; SC, subcutaneous; SR, solvent relaxation; SUVs, small unilamellar vesicles; $T_c$, transition temperature; $T_H$ cells, T-helper cells; $T_{reg}$ cells, regulatory T cells; Trp, tryptophan; vWF, von Willebrand Factor; HA, Hemophilia A.

Factor VIII (FVIII) is a 280 KDa, multidomain glycoprotein synthesized predominantly in the liver. It is made up of a light chain and a heavy chain, held together non-covalently by a divalent cation. Full length FVIII has 2332 amino acids distributed in 6 domains, namely NH2-A1-A2-B-A3-C1-C2-COOH. The heavy chain, of about 90-200 KDa, consists of A1-A2-B, while the 80 KDa light chain, consists of A3-C1-C2. The domains are interrupted by short segments of Asp and Glu; these acidic domains have been named a1, a2 and a3.

In an effort to explore the ability of FVIII-PS complexes to induce tolerance using a Reverse/Inverse Vaccination strategy, a total of forty-six naïve hemophilic female mice were used for this study. The animals were divided into six groups with each group containing 7-8 animals. The animals were administered once-a-week subcutaneous injections either of 5 IU of free FVIII or FVIII complexed with PS liposomes, PC liposomes, PG liposomes or administered with dexamethasone. A low dose of Dexamethasone (200 ng/inj) was used so as not to make the animals severely immuno-compromised, but sufficient to act as a general immunosuppressant. On the sixth week, all animals were re-challenged with four weekly subcutaneous administrations of 5 IU of free FVIII. On the eleventh week, the animals were sacrificed and blood was collected, centrifuged and plasma was collected. The plasma samples were stored at −80° C. until further analysis. In order to have baseline anti-FVIII titer values before the start of FVIII re-challenge, a total of twenty-six naïve female hemophilic mice were used for the study. The animals were divided into six groups of 4-6 animals each and were administered with 5 IU either of free FVIII or FVIII-PS/PC/PG/Dex once-a-week via the subcutaneous route for four weeks. All the animals were sacrificed on the sixth week and plasma was collected and stored at −80° C. until further analysis. Later, all the plasma samples were analyzed for anti-FVIII total and neutralizing antibody titers by using ELISA and aPTT (activated partial Thromboplastin time) assays respectively.

Lipid formulation for Reverse/Inverse Vaccination Strategy. The molar ratio for PS complex (PC:PS: 70:30), PC complex (PC: 100) and PG 30 complex (PC:PG 70:30) was used. Optimal concentration of 30 mol % was chosen for the following reasons; For PS higher than 30% promote vesicle aggregation and cochleation in the presence of Calcium ions. The PS concentration lower than 30%, substantially reduced association efficiency of the protein.

Reverse/Inverse Vaccination. Naïve hemophilic mice (20 females) aged between 6-12 weeks old were used for the study. The animals were equally divided into five groups. Each group received four weekly injections of 10 IU of free FVIII (Advate®, Baxter, Deerfield, Ill., USA; 1500 IU/vial; activity 1 ug=~7 IU of FVIII) or FVIII-PS/PC/PG30 via the subcutaneous route. The fifth group was kept untreated and served as the 'naïve' group. On the sixth week, all animals were sacrificed and their spleens were collected. The twenty spleens were homogenized individually in 10 ml of RPMI-1640 media present in a petri dish using a pestle. This procedure was carried out in a cell-culture hood. The homogenized suspension was filtered through 100 um diameter pore-sized cell strainer (BD Biosciences, Bedford, Mass., USA) into 10 ml conical tubes. The tubes were centrifuged at 300 g for 10 min at 4° C. The supernatants were discarded and the cell pellets re-suspended in 1 ml of RPMI-1640.

CD4+CD25+ T-cell isolation. Total lymphocyte count for each spleen cell suspension was determined by using the BC 2800 Vet Auto Hematology Analyzer (Mlndray, Mahwah, N.J., USA) instrument. Accordingly, a volume corresponding to $1\times10^7$ total lymphocytes from each of the twenty tubes was taken for CD4+CD25+ T-cell isolation procedure using a CD4+CD25+ T-cell isolation kit (Miltenyi Biotec, Cambridge, Mass., USA) and following the manufacturer's protocol. Upon isolation, the cells were counted by the BC 2800 Vet Auto Hematology Analyzer instrument.

Adoptive Transfer Study. Twenty naïve male hemophilic mice were utilized for this study. $0.1\times10^6$ CD4+CD25+ T-cells isolated from each of the previously described twenty samples were adoptively transferred into twenty corresponding male mice via the penile vein. After a 48 h wait period, all the animals were immunized with four weekly subcutaneous injections of 1 ug of free FVIII/injection. Two weeks after the last injection, all animals were sacrificed and blood was collected via cardiac puncture. After centrifuging at 5,000 g for 5 min at 4° C., the supernatant plasma was collected and stored at −80° C. until further analysis. Later, the twenty samples were analyzed for anti-FVIII total and neutralizing antibodies using ELISA and aPTT assays respectively.

Determination of neutralizing antibodies by aPTT assay. All the plasma samples were analyzed for anti-FVIII neutralizing antibody titers by aPTT assay following Nijmegen's modified Bethesda assay. Briefly, a reference standard curve was prepared by measuring the clotting time of serial dilutions of TriniCheck Level 1 normal pooled human plasma. A plot of natural logarithm of FVIII activity v/s clotting time in seconds provided the standard curve and the data was fitted to a straight line equation. Subsequently, all plasma samples initially kept at −80° C. were thawed on ice. Serial dilutions of the samples were made using TriniCLOT FVIII deficient plasma. The serially diluted samples were incubated with normal pooled human plasma in a 1:1 ratio at 37° C. for 2 h. The samples were then added to aPTT assay cuvettes and clotting time was measured upon addition of Platelin-L and $CaCl_2$ reagents. The serial dilution that decreased the Factor VIII activity by 50% when compared to the reference standard curve was considered as the titer value for that sample.

Determination of total binding antibodies by ELISA. Anti-FVIII total binding antibody titers were determined by ELISA assay. 50 ul of 2.5 ug/ml of free FVIII in antigen coating buffer (0.2 M $Na_2CO_3$, pH 9.6) was added to each of the 96-well NUNC maxisorp micro-plate. The plate was sealed with lid and parafilm and incubated at 4° C. overnight. Next day, serial dilutions of plasma samples were prepared in blocking buffer (2.7 mM KCl, 140 mM NaCl, 1.8 mM $KH_2PO_4$, 10 mM $Na_2HPO_4.2H_2O$, 1% w/v BSA and pH 7.4) and kept on ice. Alongside, serial dilutions of ESH8 anti-FVIII antibody were also prepared in blocking buffer to be used to prepare a reference standard curve and kept on ice. The plate was washed six times with wash buffer (2.7 mM KCl, 140 mM NaCl, 1.8 mM $KH_2PO_4$, 10 mM $Na_2HPO_4.2H_2O$, 0.05% w/v Tween 20 and pH 7.4) using a Tecan Hydroflex plate washer. 200 ul/well of Blocking buffer was added and the plate was incubated for 2 hr at room temperature. Later, the plate was washed six times with wash buffer and the serially diluted samples of reference standard and plasma samples were added in triplicate (50 ul/well) and the plate was incubated at 37° C. for 1 hr.

Afterwards, the plate was washed as described previously and 50 ul/well of 1:1000 dilution of goat anti-mouse Ig-AP detection antibody in blocking buffer was added to each well and the plate was incubated for 1 hr at room temperature. The plate was then washed as described previously and 100 ul/well of 1 mg pNPP/ml substrate in 1× Diethanolamine buffer was added and plate was incubated for 30 min at room temperature in dark. 100 ul/well of 3N NaOH stop solution was added to stop the reaction and the absorbance was read at 405 nm using a plate-reader.

Immunogenicity studies were conducted in FoxP3-GFP knock-in hemophilia A mice model as a read out for Treg Animals (n=6) received 4 weekly subcutaneous injections of either the Free FVIII or FVIII-PS lipid complexes (1 ug/injection). Animals were sacrificed 2 weeks after the last injection and the spleen and mesenteric lymph nodes were isolated and analyzed for green fluorescence protein using flow cytometry (FACS Calibur). The dot plots generated were analyzed by Cell quest software provided by the manufacturer. The CD4+ T-cells were gated for GFP detection and lymphocyte counts above 20% of total lymphocytes were analyzed for Green fluorescence protein. The average (n=6) baseline expression of GFP in naïve animals was subtracted from treatment groups.

Figure 6A:
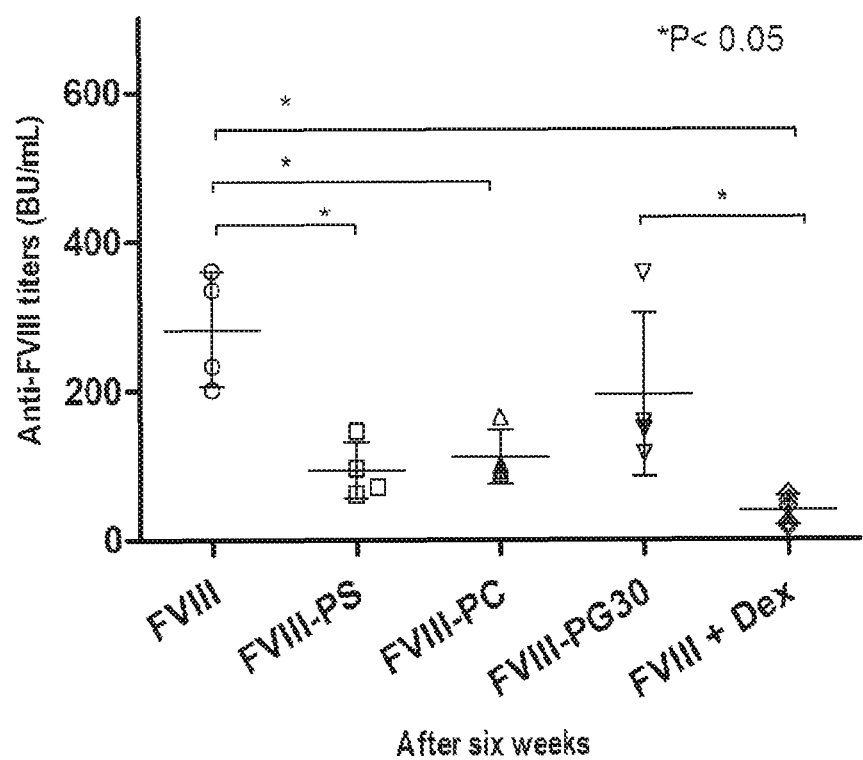
FIG. 6 a) Sixth week anti-FVIII inhibitory titer levels following four weekly subcutaneous injections of free FVIII or FVIII-PS, FVIII-PC, FVIII-PG or Dexamethasone (Dex) to naïve hemophilic mice. Dex is a general immuno-suppressant. The naïve Hemophilia A (HA) mice were divided into separate groups and were administered once-a-week subcutaneous injection of the following: 5 (five) International units (IU) of Factor VIII (FVIII) alone; 5 (five) IU of FVIII complexed with PS liposomes (30% PS and 70% PC in molar ratio); 5 (five) IU of FVIII complexed with PC liposomes (100% PC); 5 (five) IU of FVIII complexed with Phosphatidylglycerol (PG) liposomes (30% PG and 70% PC in molar ratio (PG30); 5 (five) IU of FVIII and 200 nanogram (ng) of Dexamethasone (Dex). Data was obtained 6 weeks after the last sc injection of the various compositions.
FIG. 6b): Eleventh week inhibitory titer levels for FVIII re-challenge (i.e. subsequent challenge with free FVIII) following administrations as described in FIG. 6a; Animals primed with FVIII-PS were hypo-responsive to subsequent free FVIII exposure.
FIG. 6c): Sixth and eleventh week anti-FVIII inhibitory titer levels shown together.
Figure 6B:
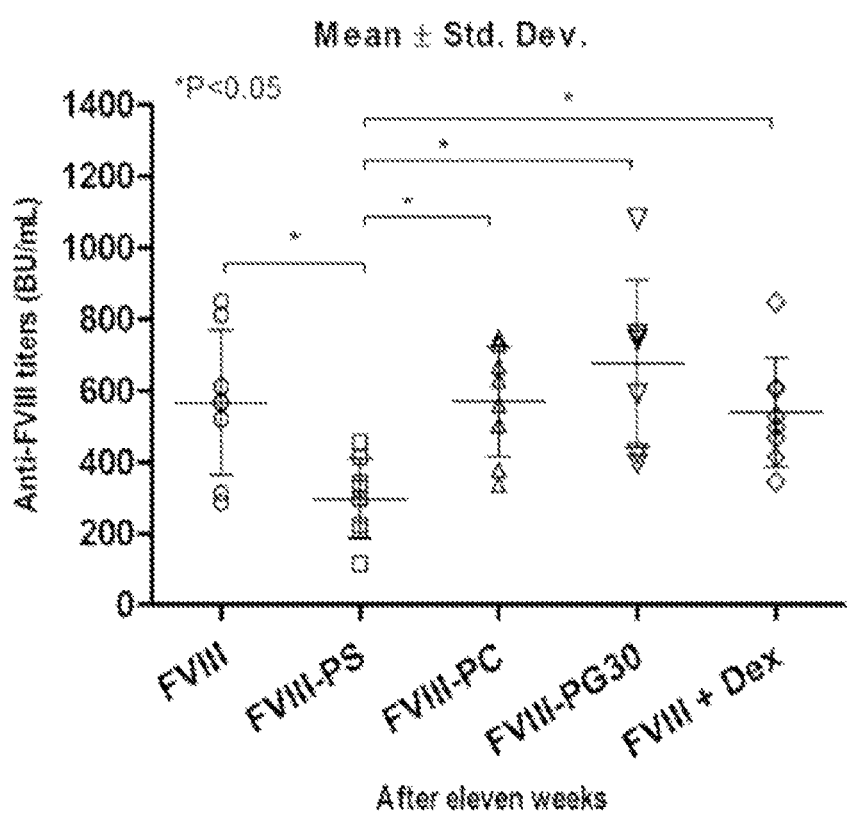
Figure 6C:
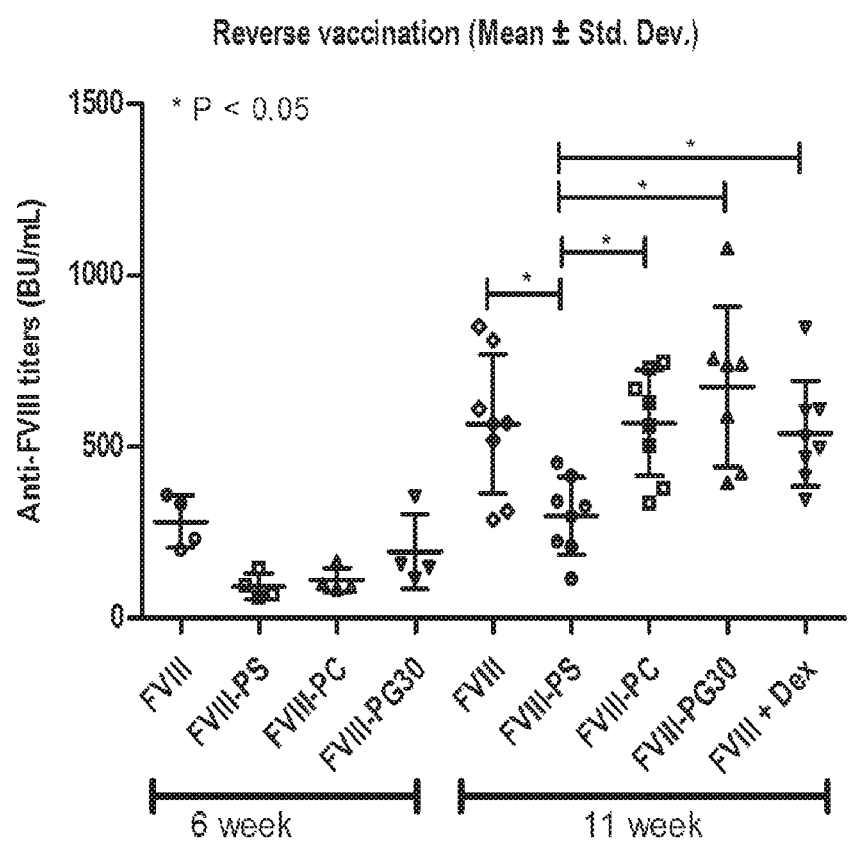

If PS presents FVIII in a tolerogenic manner to DC, pre-exposure should lead to immunological hypo-responsiveness to FVIII re-challenge. Thus, the experimental design involved pre-exposure of HA mice to FVIII-lipid complex and the antibody response was measured following re-challenge with FVIII. Levels of anti-FVIII Nabs in animals pre-immunized either with free FVIII (567±72) or FVIII-PC (570±55 SEM) or FVIII-PG (677±88 SEM) or FVIII+Dex (539±34 SEM) showed comparable levels of anti-FVIII Nabs (FIG. 6a). In contrast, animals pre-treated with FVIII-PS showed significantly reduced FVIII Nab levels (298±40 SEM). Further, to determine the rate of progression of immune response after re-challenge, a correlation of the mean anti-FVIII Nab titers measured on the sixth and eleventh week for each group was performed (FIGS. 6b and 6c). After administration/priming of FVIII or FVIII PS/PC/PG/Dex, the Nab titer levels were measured at the end of sixth week. Naïve HA mice that received free FVIII alone showed high levels of anti-FVIII Nab titers (282±39 SEM). In comparison, significant reduction in baseline anti-FVIII Nab titers on the sixth week was observed in animals that were immunized with FVIII-PS (93±19 SEM) or FVIII-PC (111±18 SEM). FVIII complexed with anionic PG liposomes produced Nab levels (195±55 SEM) statistically comparable to the levels observed in free FVIII immunized animals. Further, animals that were immunized with FVIII in the presence of low doses of Dex (immunosuppressant) developed relatively minimal levels of anti-FVIII antibodies (39±9 SEM). However, the Nab lowering beneficial effect observed with Dex and PC pre-treatment on the sixth week did not extend after their administration was stopped (post sixth week). The data clearly demonstrate that only PS was able to significantly delay the progress of FVIII immune response even after the PS exposure was stopped on the sixth week. Thus, the results indicate that pre-exposure of FVIII-PS leads to hypo-responsiveness towards FVIII re-challenge. Based on these studies, the reverse/inverse vaccination of the present invention can be used to reduce unwanted immunogenic response against therapeutic proteins. Unlike conventional vaccination approaches, this approach de-sensitizes the patient to an antigen and thus these patients will be unable to immunologically respond to the protein.

During the reverse vaccination strategy, it is desirable that the immunization should not interfere with the ability of the immune system to mount immune response against other antigens and pathogens. In order to investigate the antigen specificity and effect of immunization on the systemic immune suppression, another foreign antigen; ovalbumin (Ova) was concomitantly administered with either FVIII or FVIII-PS/PC complexes, but at a distant anatomical site. Anti-FVIII Nab titers in animals that were administered with FVIII-PS (100±17 SEM) were significantly lower than free FVIII (375±60 SEM) immunized group. Mice that were immunized with only Ova had no anti-FVIII Nabs. However, all animals showed statistically comparable anti-Ova titers irrespective of the treatment group. As the animals responded to Ova by developing comparable titers, the data suggests that FVIII-PS does not render systemic immunosuppressive effects and the antigen-specific hypo-responsiveness could be achieved by presenting antigen of interest with PS lipid.

Figure 7:
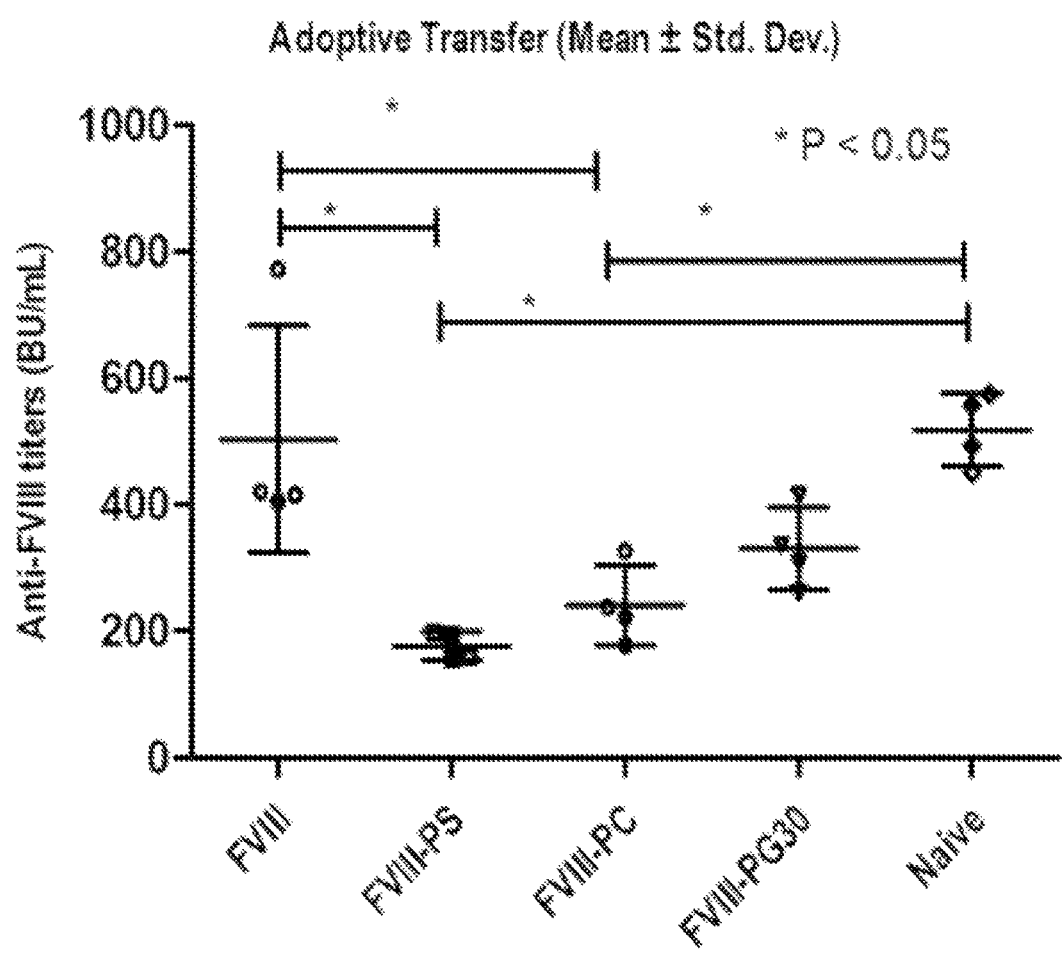
FIG. 7: Anti-FVIII inhibitory titer levels following FVIII challenge in naïve hemophilic recipient mice following adoptive transfer of CD4+CD25+ T cells taken from hemophilic donor mice immunized with FVIII and FVIII lipid complex. Sixth week post re-challenge plasma was analyzed for anti-FVIII neutralizing antibody (Nab) titers (Mean±SEM) and expressed in BU/ml. *P<0.05 was considered as a statistically significant difference.
Figure 8:
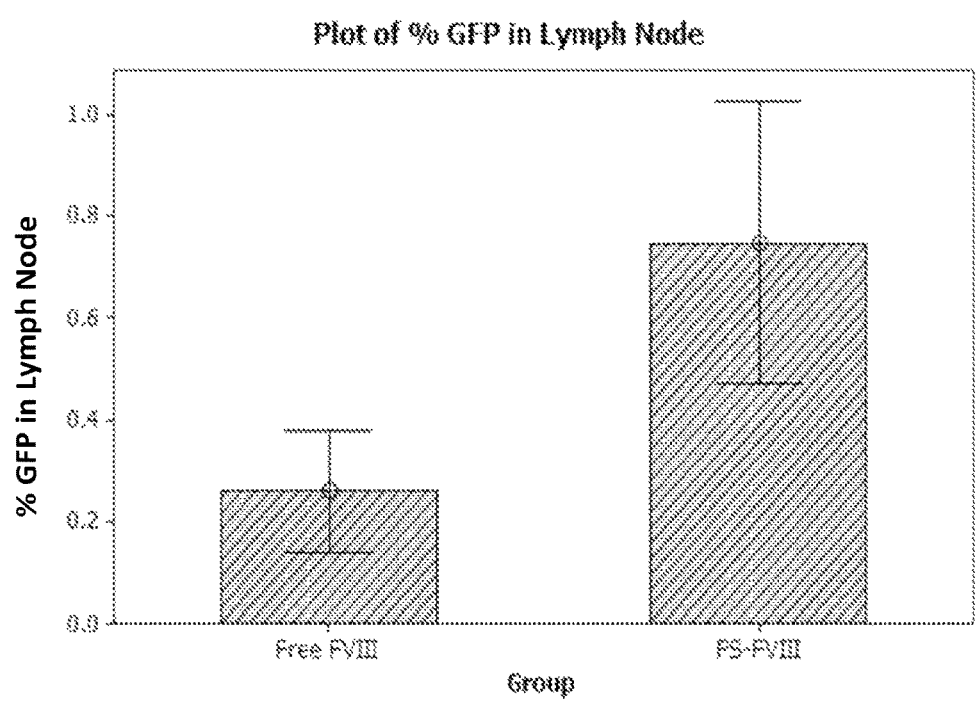
FIG. 8: Representation of the number of GFP positive cells following 4 weekly immunization of factor VIII and FVIII-PS liposomal complexes.
Figure 9:
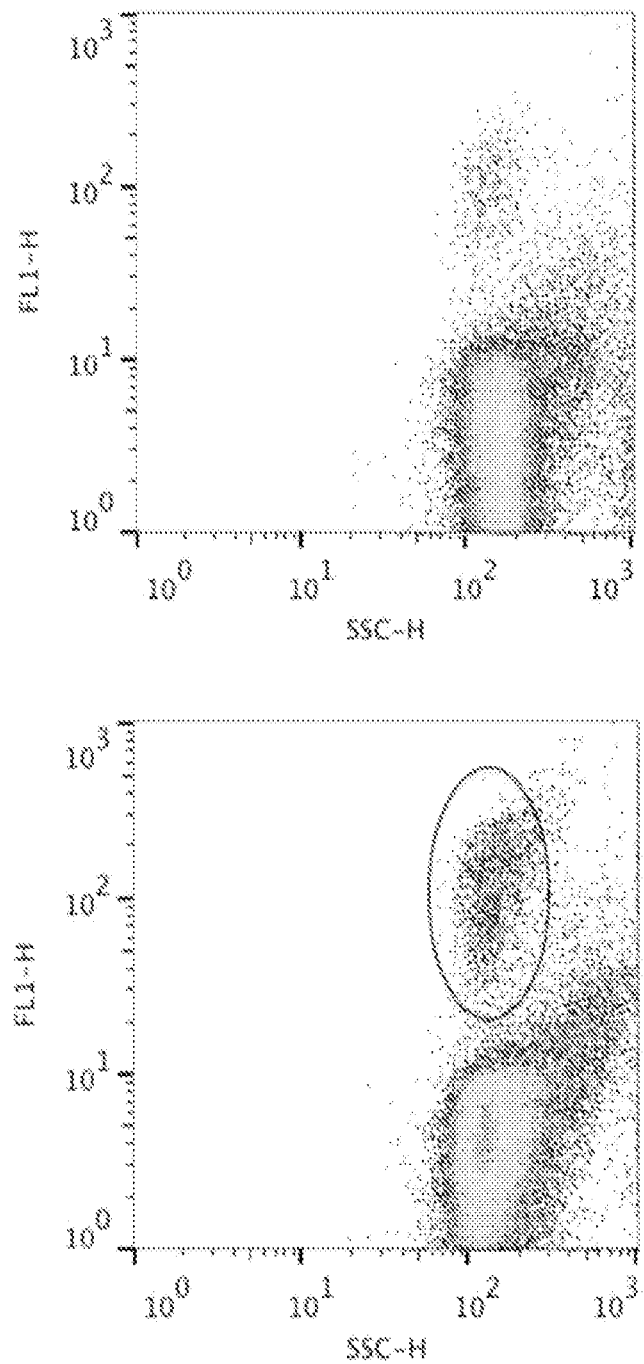
FIG. 9: Flow cytometry evaluation of Foxp3 expression in FVIII and FVIII-PS immunized animals following the Reverse/Inverse Vaccination strategy. Representation of dot plot of percentage GFP cells after gating CD4+ T cells (Lymphocytes) for Factor VIII (upper panel) and PS-Factor VIII (lower panel).

The generation of peripherally induced regulatory T-cells (iTregs) can regulate immune response by suppressing effector cells. The involvement of iTregs in inducing hyporesponsiveness towards FVIII is supported by our adoptive cell transfer studies. Upon adoptive transfer of $CD4^+CD25^+$ T-cells from FVIII or FVIII-PS/PG immunized or naïve donor mice, recipient mice were challenged with free FVIII and anti-FVIII Nab titers were measured (FIG. 7). Mice that received $CD4^+CD25^+$ T-cells from FVIII-treated or T-cells from naïve (unimmunized) mice elicited robust FVIII immune response (Nab titers of 503±90 SEM and 519±29 SEM respectively). In comparison, mice that received $CD4^+CD25^+$ T-cells from FVIII-PS treated donor mice exhibited significantly reduced anti-FVIII Nab titers (177±11 SEM). However, $CD4^+CD25^+$ T-cells transferred from mice treated with FVIII associated with another negative charge PG lipid (FVIII-PG) failed to significantly reduce Nab titers (331±32 SEM). These results indicate that the FVIII-PS induced hypo-responsiveness is transferrable and that $CD4^+CD25^+$ T-cells may be involved in the generation of this hypo-responsiveness.

In order to determine whether Factor VIII-PS mediated hypo-responsiveness is immunologically significant, the spleen of the animals that were subjected to prolonged immunization with Factor VIII-PS was analyzed for regulatory markers such as induction of regulatory T-cells in periphery. Green Fluorescence Protein (GFP)-FoxP3 knocked-in $FVIII^{-/-}$ mice were used. Mice were immunized with FVIII and FVIII-lipid complex and green fluorescence protein expression was used as a read out for FoxP3 expression—a biomarker for Treg. A lipid-mediated reduction in immunogenicity would involve presenting antigen in a tolerogenic manner to antigen presenting cells, such as Dendritic cells. This interaction converts dendritic cells into tolerogenic dendritic cells with reduced expression of co-stimulatory signals (CD40). In the presence of regulatory cytokines TGF-beta and IL-10, promote the generation of regulatory T-cells (Treg). A Cd4+ T-cell types acquire the regulatory ability by Foxp3 expression. FoxP3 is a biomarker for Treg. This is supported by the data provided herein. As is clear from FIG. 8, the animals that received FVIII-PS containing lipid particles showed higher GFP expression compared to free Factor VIII treatment group. The mean number of GFP-expressing cells for FVIII-PS treatment group (4.04±SEM, n=6) is higher than observed for FVIII group (3.19±SEM, n=5) that showed comparable GFP expression as that observed in naïve animals. A representative dot plots are shown and the GFP positive region is highlighted in FIG. 9. The dot plots generated were analyzed by Cell quest software provided by the manufacturer. The CD4+ T-cells were gated for GFP detection and lymphocyte counts above 20% of total lymphocytes were analyzed for Green fluorescence protein. The average (n=6) baseline expression of GFP in naïve animals was subtracted from treatment groups.

Thus, exposure of FVIII in the presence of PS induce hypo-responsiveness that is likely to be mediated by FoxP3-Treg mechanism. The animals that received FVIII-PS containing lipid particles showed higher GFP expression compared to free FVIII immunized group. It is considered that the PS-mediated hypo-responsiveness towards FVIII may likely be due to induction of tolerance possibly via Treg mechanism.

Example 3

This example describes the preparation of liposome complexes with another protein, acid α-glucosidase (GAA) peptide 340-352, which has previously been shown to be the most prominent of three T-cell epitopes involved in the immune response to intravenously administered recombinant human GAA (rhGAA). The peptide was associated with a phosphatidylserine (PS) liposome to tolerize GAA knockout mice and could be replaced with GAA or lipidic GAA. This GAA peptide is 13 amino acids long containing amino acids 339-352 of the GAA sequence. The tryptophan residue at position 339 was added to the T-cell epitope sequence found by Nayak et al. (Molecular Genetics and Metabolism 2012, 106 (2), 189-195) in order for us to detect the peptide by fluorescence. PS liposomes containing this peptide were prepared as follows. A lipid film containing 30% PS and 70% 1,2-Dimyristoyl-sn-Glycero-3-Phosphocholine (DMPC) was prepared. The film was rehydrated at 37° C. with peptide in a calcium containing TRIS buffer (300 mM NaCl, 25 mM TRIS, 5 mM $CaCl_2$, pH 7.0) at a 1:250 peptide to lipid molar ratio. The final concentration of peptide in the preparation is 100 μg/ml. Once the film was rehydrated, the preparation underwent three cycles consisting of four minutes of heating at 37° C. followed by one minute of gentle swirling by hand. Then the preparation was extruded through two 80 nm-polycarbonate filters twenty times using a nitrogen gas extruder. This resulted in liposomes that were approximately 100 nm. These complexes were used to immunize animals.

The preceding description provides specific examples of the present invention. Those skilled in the art will recognize that routine modifications to these embodiments can be made which are intended to be within the scope of the invention.

The invention claimed is:

1. A method for inducing in an individual immune tolerance to a therapeutic protein comprising the steps of:

a) administering multiple times to the individual a first composition comprising the protein complexed to liposomes comprising i) phosphatidylserine (PS) and phosphatidylcholine (PC), or ii) phosphatidylserine (PS), phosphatidylinositol (PI), and phosphatidylcholine (PC);

b) after waiting for at least 4 days after the last administration of the first composition administering to the individual a second composition comprising the protein, wherein the second composition is free of liposomes.

2. The method of claim 1, wherein the liposomes of the first composition comprise PS:PC in a ratio of 10:90 to 50:50 mol %.

3. The method of claim 1, wherein the liposomes of the first composition comprise PS:PC in a ratio of 30:70 mol %.

4. The method of claim 1, wherein the liposomes of the first composition comprise PS:PI:PC in a ratio of 30:30:40 mol % and, optionally, further comprise 5-15% cholesterol, wherein the cholesterol amount is a molar percent of the combined PS, PI and PC.

5. The method of claim 1, wherein the protein is Factor VIII.

6. The method of claim 1, wherein the second composition is administered after waiting for at least 7 days after the last administration of the first composition.

7. The method of claim 1, wherein the priming compositions is administered via the subcutaneous route.

8. The method of claim 1, wherein the development of immune tolerance is detectable by down-regulated expression of co-stimulatory signals on dendritic cells, lowered CD4+ T-cell proliferation and/or induced secretion of TGF-β and IL-10.

\* \* \* \* \*